(12) United States Patent
Chung et al.

(10) Patent No.: US 8,501,689 B2
(45) Date of Patent: *Aug. 6, 2013

(54) GROWTH FACTOR-MIMICKING PEPTIDES AND USES THEREOF

(75) Inventors: Yong-Ji Chung, Yongin-si (KR); Young Deug Kim, Siheung-si (KR); Eun Mi Kim, Gunpo-si (KR); Jun Young Choi, Gunpo-si (KR)

(73) Assignee: Caragen Co., Ltd., Gunpo-si (KR)

( * ) Notice: Subject to any disclaimer, the term of this patent is extended or adjusted under 35 U.S.C. 154(b) by 281 days.

This patent is subject to a terminal disclaimer.

(21) Appl. No.: 12/936,962

(22) PCT Filed: Mar. 6, 2009

(86) PCT No.: PCT/KR2009/001134
§ 371 (c)(1),
(2), (4) Date: Oct. 8, 2010

(87) PCT Pub. No.: WO2009/125925
PCT Pub. Date: Oct. 15, 2009

(65) Prior Publication Data
US 2011/0160131 A1    Jun. 30, 2011

(30) Foreign Application Priority Data
Apr. 11, 2008   (KR) .................. 10-2008-0033687

(51) Int. Cl.
A61K 38/18       (2006.01)
A61P 17/02       (2006.01)
A61K 38/00       (2006.01)
A61K 38/08       (2006.01)

(52) U.S. Cl.
USPC ..................... 514/9.2; 514/9.4; 514/21.6

(58) Field of Classification Search
None
See application file for complete search history.

(56) References Cited

U.S. PATENT DOCUMENTS
4,816,561 A * 3/1989 Todaro ................... 530/324

FOREIGN PATENT DOCUMENTS
EP        0 190 018    * 8/1998

OTHER PUBLICATIONS

Roberts et al. Chemistry for peptide and protein PEGylation. Advanced Drug Delivery Reviews, 2002, vol. 54, pp. 459-476.*
N-Terminal Acetylation and C-terminal Amidation of Peptides. Technical Information—THERMO. Thermo Electron GmbH, Germany. 2004, 2 pages.*
GenBank Accession No. EDK99158.1 "Transforming Growth Factor Alpha, Isoform CRA_a [*Mus musculus*]," Jun. 7, 2007.
International Search Report from International Application No. PCT/KR2009/001134, dated Oct. 21, 2009 (date of completion of search) and Oct. 22, 2009 (date of mailing of report).

* cited by examiner

Primary Examiner — Marcela M Cordero Garcia
(74) Attorney, Agent, or Firm — Clark & Elbing LLP

(57) ABSTRACT

The present invention relates to a growth factor-mimicking peptide having an activity of the growth factor, and a composition and a method for improving skin conditions or for treating a wound using the same. The growth factor-mimicking peptides of this invention have identical functions or actions to natural-occurring human growth factor, and much better stability and skin penetration potency than natural-occurring growth factor. In these connections, the composition comprising the peptides of this invention can exhibit excellent efficacies on the treatment, prevention and improvement of diseases or conditions demanding growth factor activities. In addition, excellent activity and stability of the peptides of this invention can be advantageously applied to pharmaceutical compositions, quasi-drugs and cosmetics.

4 Claims, 13 Drawing Sheets

Fig. 1

Amino acid sequence of KGF and peptide 1

CNDMT PEQMA TNVNC SSPER HTRSY DYMEG GDIRV RRLFC RTQWY LRIDK
RGKVK GTQEM KNNYN IMEIR TVAVG IVAIK GVESE FYLAM NKEGK LYAKK
ECNED CNFKE LILEN HYNT Y ASAKW THNGG EMFVA LNQKG IPVRG KKTKK
EQKTA HFLPM AIT

Selected peptide 1: YKSKKGGWTH

Amino acid sequence of aFGF and peptide 2

AEGEI TTFTA LTEKF NLPPG NYKKP KLLYC SNGGH FLRIL PDGTV DGTRD
RSDQH IQLQL SAESV GEVYI KSTET GQYLA MDTDG LLYGS QTPNE ECLFL
ERLEE NHYNT YISKK HAEKN WFVGL KKNGS CKRGP RTHYG QKAIL FLPLP
VSSD

Selected peptide 2: YISKKHAGKNWF

Amino acid sequence of TGF-α and peptide 3 and 4

VVSHF NDCPD SHTQF CFHAT CRFLV HEDKP ACVCH SGYVG ARCEH ADLLA

Selected peptide 3: DSHTQYCFHGT
Selected peptide 4: GYVGVRCEAADLDA

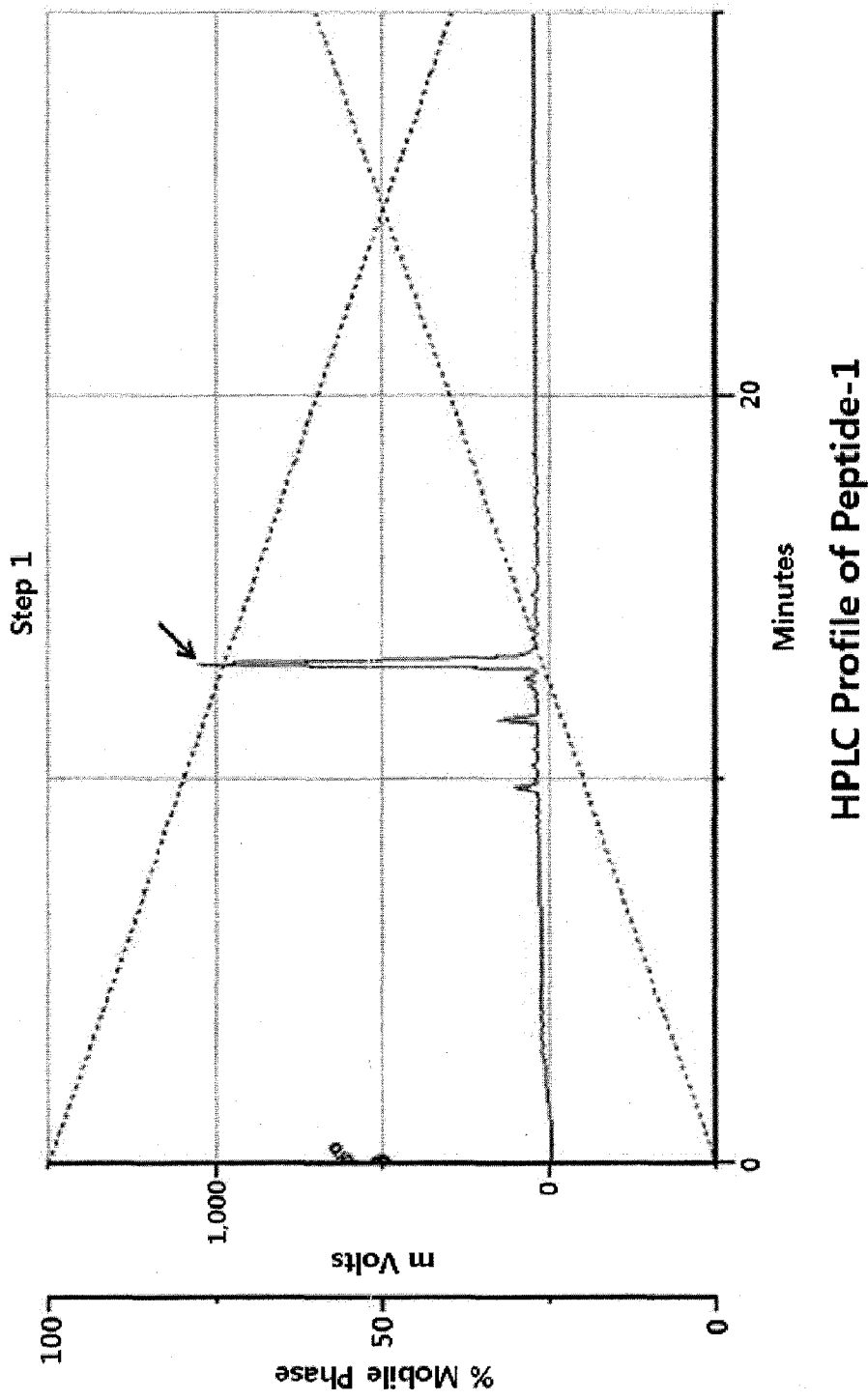

Fig. 8
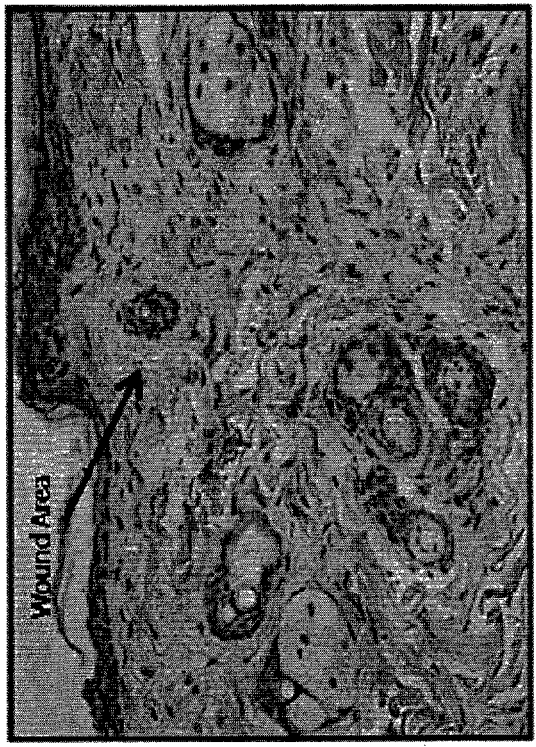
Peptide Complex Nanosome Hydrogel
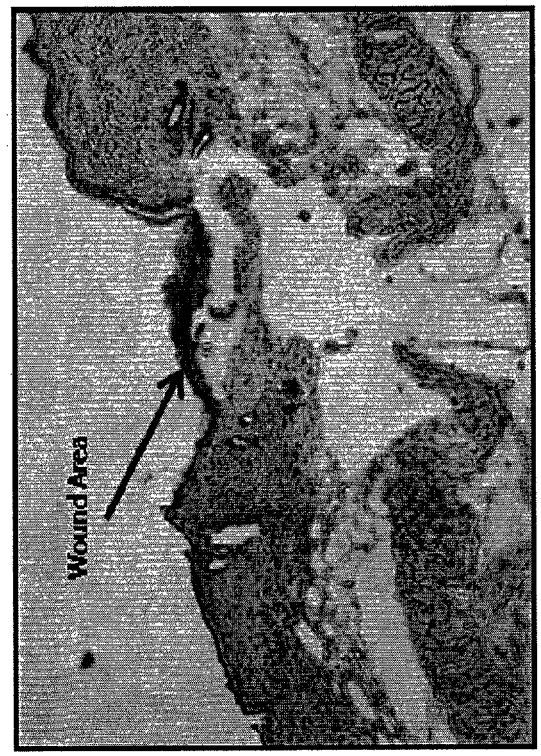
Control Hydrogel only

GROWTH FACTOR-MIMICKING PEPTIDES AND USES THEREOF

CROSS-REFERENCE TO RELATED APPLICATIONS

This application is the U.S. national stage filing under 35 U.S.C. § 371 of international application PCT/KR2009/001134, filed Mar. 6, 2009, which claims benefit of Korean Patent Application 10-2008-0033687, filed Apr. 11, 2008.

BACKGROUND OF THE INVENTION

1. Field of the Invention

The present invention relates to a growth factor-mimicking peptide having an activity of the growth factor, and a composition and a method for improving skin conditions or for treating a wound using the same.

2. Description of the Related Art

Growth hormones secreted from human pituitary glands are known to be directly associated with cell growth and differentiation, and thereby affect a variety of cellular responses, for example including facilitation of growth and development of cartilage or bone, restoration of internal organs such as muscle or liver, regeneration of wounds, and immune responses against infection. Moreover, it has been reported that an amount of growth hormones is gradually reduced due to aging, and the level of growth hormones in a group aged 60 to 69 years is only ¼ compared with that in a group aged 20 to 29 years. Therefore, there have been actively utilized anti-aging hormone therapies which supplement insufficient growth hormones.

Growth hormone is directly bound to a growth hormone receptor in a cell, or induces a secretion of insulin-like growth factor I (IGF-1), leading to activate cellular signal molecules such as JAKs (Janus kinases)/STATs (Signal Transducers and Activators of Transcription), MAPKs (mitogen-activated protein kinases), or PI3K (phosphatidyl-3 kinase). Consequently, it has been supposed that growth hormones promote growth of fibroblasts in hair follicles or skin, and inhibit apoptosis via regulation of a blc-2-like gene, bcl-w. These activities of growth factors have been elucidated by numerous researchers, and various companies have attempted commercialization of growth factors due to their utilization.

Fibroblast growth factor (FGF) is classified into two types, i.e., acidic FGF (aFGF) and basic FGF (bFGF), and both have been reported to be isolated and purified from mammalian brain (Thomas and Gimenez-Gallego, *TIBS* 11:81-84 (1986)).

Among growth factors, acidic FGF (aFGF) is a protein consisting of 154 amino acids, which is one of major molecules in a biomedical research for tissue restoration and wound healing, for example an activity to regulate growth of animal cells, especially human cells. A mitogen for an acidic fibroblast was first found by Trowell et al. (*J. Exp. Biol.* 16: 60-70 (1939)) and Hoffman (*Growth* 4: 361-376 (1940)). In addition, pituitary extracts were found to have a potent mitogenic activity for fibroblasts (Amelin, *Proc. Natl. Acad. Sci. USA* 70: 2702-2706 (1973)).

Purified aFGF allows numerous cell lines to synthesize DNA and to divide as responses to stimuli, which include primary fibroblasts, vascular and corneal endothelial cells, chondrocytes, myeloblasts, myoblasts, smooth muscle cells, neuroglial cells and neuroblasts (Each et al., *Proc. Natl. Acad. Sci. USA* 82: 6507-6511 (1985); Kuo et al., *Fed. Proc.* 44: 695 (1985); Gensburger et al., *C.R. Acad. Sc. Paris* 303: 465-468 (1986)). Additionally, aFGF not only is a strong mitogenic molecule for vascular endothelial cells but also induces in vivo growth of blood vessel (Thomas. et al., *Proc. Natl. Acad. Sci. USA* 82: 6409-6413 (1985)). The mitogenic activity of purified aFGF may be also utilized in facilitation of wound healing (Thomas, U.S. Pat. No. 4,444,760).

Meanwhile, keratinocyte growth factor (KGF) is a protein consisting of 163 amino acids, and accelerates division of epithelial cells, contributing to rapid regeneration of several wounds. KGF affects various cell types as a member of fibroblast growth factor family. KGF plays a pivotal role in treatment of cell injuries generated by several causes including adhesion between cells, cell division and aging. In addition, KGF essentially functions as a bridge between cell generations in early stage of hair growth. In addition to improvement in skin elasticity, promotion of hair growth and acceleration of wound healing, KGF may be utilized as various uses.

Likewise, transforming growth factor (TGF) is a cytokine which has an essential activity for growth and differentiation of skin cells in a deep site of skin to maintain the skin very young and health. For example, aging cells damaged may be altered to be very healthful cells with higher division activity through transformation and restoration. TGF treats damaged cells, and thus a scar formation in a tissue may be prevented. TGF binds to an EGF receptor, leading to increase synthesis of a basement membrane protein and to stimulate growth of endothelial cells. TGF may exert several efficacies besides enhancement in skin elasticity, promotion of hair growth, acceleration of wound healing and induction of anti-aging environment.

For mass production of the above-mentioned growth factors, many researchers have made intensive researches on production of the recombinant protein using *E. coli* expression systems. However, these preparations are encountered to need of time- and cost-consuming refolding process and of complex purification process to remove *E. coli*-originated contaminants. To be free from such shortcomings, growth factor-like peptides have been prepared by solid phase synthesis methods. For instance, U.S. Pat. No. 5,473,054 filed by Jameson et al. discloses that JB2 (corresponding to amino acid 29-38 of IGF-1) and JB1 (corresponding to amino acid 61-70) fragment have cell proliferation potential and the enantiomer of JB1, JB3 has inhibitory activity to IGF-1. WO 03/048192 filed by Teruo et al. teaches that each of the peptide fragment of IGF-1 consisting of amino acid 33-37 and substance-P derived tetrapeptide exerts complementary efficacy to wound healing. In addition, Kodama et al. reports that the peptide fragment of IGF-1 consisting of amino acid 50-70 has a therapeutic effect to diabetes in mice (*Autoimmunity*, 37: 481-487 (2004)).

Throughout this application, various patents and publications are referenced, and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

For developing peptides having actions identical to natural-occurring KGF, aFGF or TGF, and having more significant characteristics such as activity, skin penetration and stability than natural-occurring KGF, aFGF or TGF, the present inventors have made intensive researches. As a result, the present inventors have discovered several growth factor (GF)-mimicking peptides having excellent characteristics described above on the basis of the amino acid sequence of natural-occurring growth factors, eventually accomplishing the present invention.

Accordingly, it is one object of this invention to provide a peptide having the activity of growth factor.

It is another object of this invention to provide a composition for improving skin conditions.

It is still another object of this invention to provide a composition for treating a wound.

It is still another object of this invention to provide a method for improving skin conditions.

It is further still another object of this invention to provide a method for treating a wound.

Other objects and advantages of the present invention will become apparent from the following detailed description together with the appended claims and drawings.

In one aspect of this invention, there is provided a peptide having an activity of a growth factor (GF) and derived from GF, which comprises the amino acid sequence selected from SEQ ID NOs:1-4.

For developing peptides having actions identical to natural-occurring KGF, aFGF or TGF, and having more significant characteristics such as activity, skin penetration and stability than natural-occurring KGF, aFGF or TGF, the present inventors have made intensive researches. As a result, the present inventors have discovered several growth factor-mimicking peptides having excellent characteristics described above on the basis of the amino acid sequence of natural-occurring growth factors.

The peptide of the present invention includes the human GF-derived amino acid sequence selected from SEQ ID NOs: 1-4. Preferably, the peptide consists essentially of the amino acid sequence selected from SEQ ID NOs:1-4. Most preferably, the peptide consists of the amino acid sequence selected from SEQ ID NOs:1-4.

The term used herein "peptide" refers to a linear molecule formed by linking amino acid residues through peptide bonds.

The peptides of the invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The design of peptides according to the present invention is exemplified in FIG. 1.

The peptides of the present invention may be prepared by predicting a portion capable of binding to a receptor protein of growth factor and optimizing an amino acid sequence of the predicted portion. For instance, a portion capable of binding to a receptor protein is predicted in amino acids 100-140 of keratinocytes, amino acids 110-125 of aFGF, and amino acids 35-49 of TGF-α. Afterwards, the candidate peptides are prepared in reference with the above-mentioned amino acid sequence, and then the peptide having the most excellent activity is screened, resulting in the peptides of this invention.

SEQ ID NO:1 is derived from amino acids 120-127 of natural-occurring human KGF. SEQ ID NO:2 is derived from amino acids 111-122 of natural-occurring human aFGF. SEQ ID NO:3 and SEQ ID NO:4 are derived from amino acids 10-20 and 38-49 of natural-occurring human TGF-α, respectively.

Even though the peptides of this invention per se have higher stability than natural-occurring growth factor, their modification enables to have much higher stability. According to a preferable embodiment, the C-terminal of the peptides of the present invention is modified to have a hydroxyl group (—OH) or an amino group (—NH$_2$).

According to a preferred embodiment, the N-terminal of the peptides of the present invention is protected with a protection group selected from the group consisting of acetyl group, fluorenyl methoxy carbonyl group, formyl group, palmitoyl group, myristyl group, stearyl group or polyethylene glycol (PEG).

The modifications of peptides described above greatly increase the stability of peptides of this invention. The term used herein "stability" refers to in vivo stability and storage stability (e.g., storage stability at room temperature) as well. The protection group described above protects the peptides from the attack of protease in vivo.

In another aspect of this invention, there is provided a composition for improving skin conditions, comprising as an active ingredient the growth factor-mimicking peptide of this invention.

In still another aspect of this invention, there is provided a composition for treating a wound, comprising as an active ingredient the growth factor-mimicking peptide of this invention.

In still another aspect of this invention, there is provided a method for improving skin conditions, comprising administering to a subject a composition containing the peptide of this invention.

In further still another aspect of this invention there is provided a method for treating a wound, comprising administering to a subject a composition containing the peptide of this invention.

Since the present method comprises the growth factor-mimicking peptide of this invention as active ingredients described above, the common descriptions between them are omitted in order to avoid undue redundancy leading to the complexity of this specification.

As demonstrated in Examples below, the growth factor-mimicking peptides of the present invention having actions identical to natural-occurring growth factor (e.g., KGF, aFGF and TGF) promote the proliferation of fibroblasts and keratinocytes, and production of collagen and fibronectin. Therefore, the composition of the present invention has excellent efficacies on the improvements in skin conditions.

According to a preferable embodiment, the composition of this invention may be utilized in improvements in skin conditions such as improvement in wrinkle or skin elasticity, prevention of skin aging, prevention of hair loss, promotion of hair growth, improvement in skin moisture, removal of dark spots or treatment of acne.

Interestingly, the growth factor-mimicking peptides of the present invention have excellent wound healing effects as demonstrated in Examples below.

According to a preferable embodiment, the composition of this invention may be utilized in a closed wound and open wound. For example, the closed wound includes contusion or Burise, and the open wound includes abrasion, laceration, Avulsion, penetrated wound and gun shot wound.

The present composition may be prepared as a pharmaceutical or cosmetic composition.

According to a preferred embodiment, the composition is a pharmaceutical composition comprising (a) a pharmaceutically effective amount of the growth factor-mimicking peptide of the present invention; and (b) a pharmaceutically acceptable carrier.

The term used herein "pharmaceutically effective amount" refers to an amount enough to show and accomplish efficacies and activities of the peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, subcutaneous, intramuscular, intraperitoneal, local or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.001-100 mg/kg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition comprising (a) a cosmetically effective amount of the growth factor-mimicking peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these substances.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as bFGF modifiers as active ingredients and carriers. The non-limiting examples of auxiliaries include antioxidants, stabilizers, solubilizers, vitamins, colorants, odor improvers or mixtures of these substances.

The features and advantages of the present invention will be summarized as follows:

(i) The growth factor-mimicking peptides of the present invention possess identical functions or activities to natural-occurring human growth factor;

(ii) The peptides of the present invention are much higher stability and skin penetration potency than natural-occurring growth factor;

(iii) Therefore, the composition comprising the peptide exhibits excellent treatment, prevention or improvement efficacies on diseases or conditions demanding growth factor activities; and (iv) Excellent activity and stability of the peptides of this invention can be advantageously applied to pharmaceutical compositions, quasi-drugs and cosmetics.

BRIEF DESCRIPTION OF THE DRAWINGS

FIG. 1 represents the amino acid sequence of naturally-occurrinq growth factors and selected regions for preparing peptides of the invention (SEQ ID NOs:5, 1, 6, 2, 7, 3, and 4, as listed from the top of the figure to the bottom).

FIG. 2c represents a high performance liquid chromatography analysis of the peptide of SEQ ID NO:3 prepared in Example.

FIG. 8 is a tissue image to observe wound healing effects in wound tissue of Balb/C mice after a hydrogel containing the peptides of the present invention is treated to wound area of Balb/C mice for 10 days.

Figure 2A:
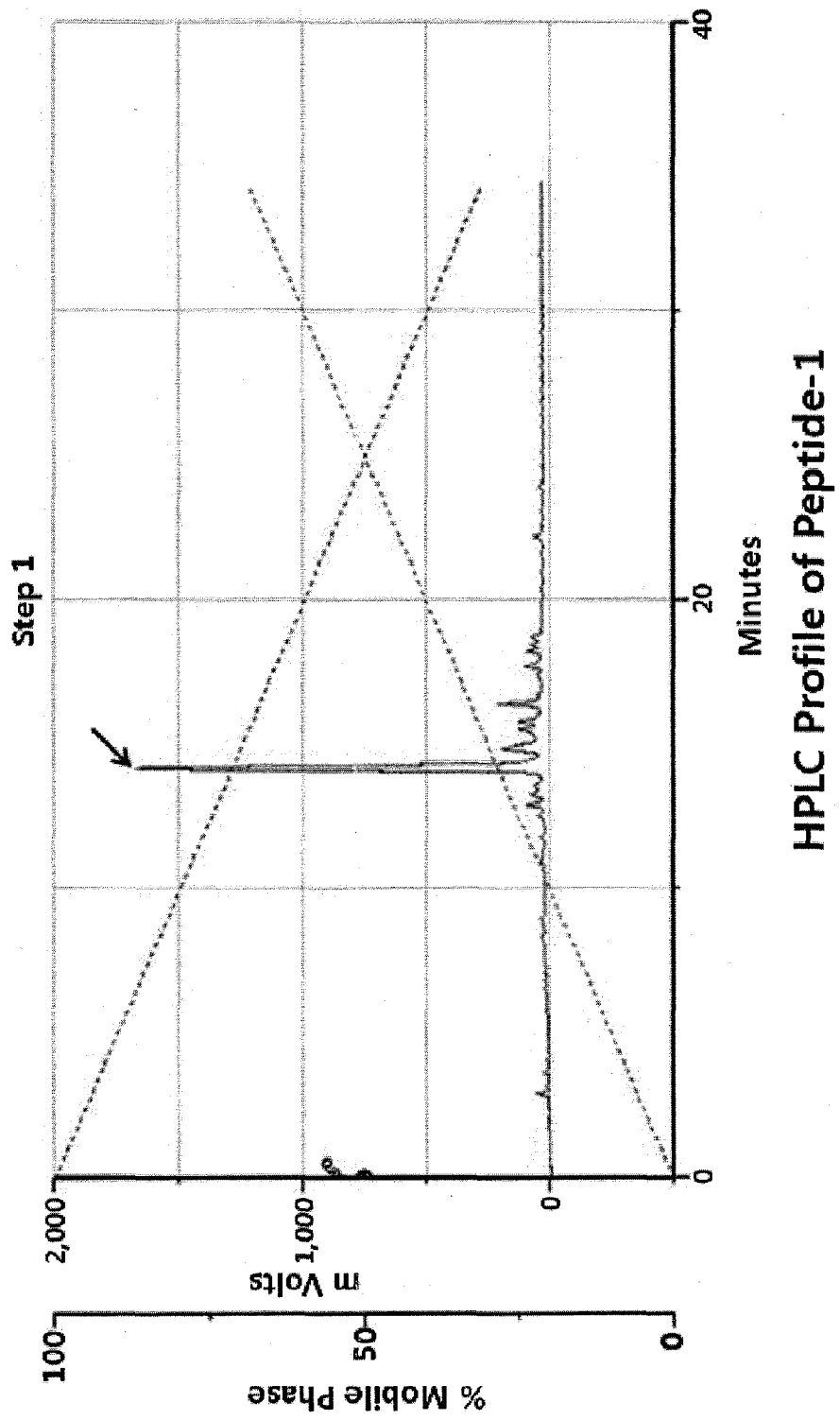
FIG. 2a represents a high performance liquid chromatography analysis of the peptide of SEQ ID NO:1 prepared in Example.
Figure 2B:
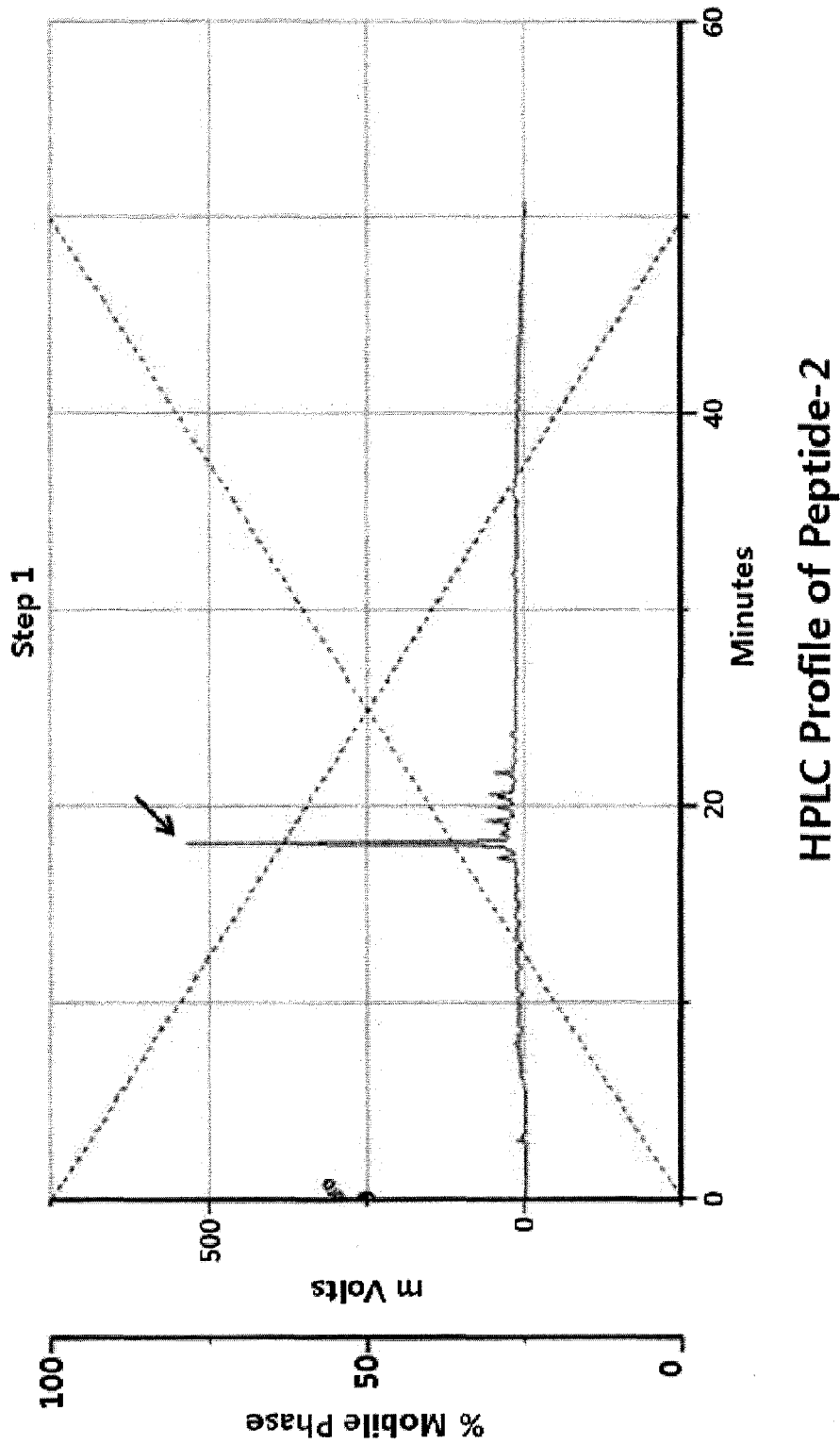
FIG. 2b represents a high performance liquid chromatography analysis of the peptide of SEQ ID NO:2 prepared in Example.
Figure 2D:
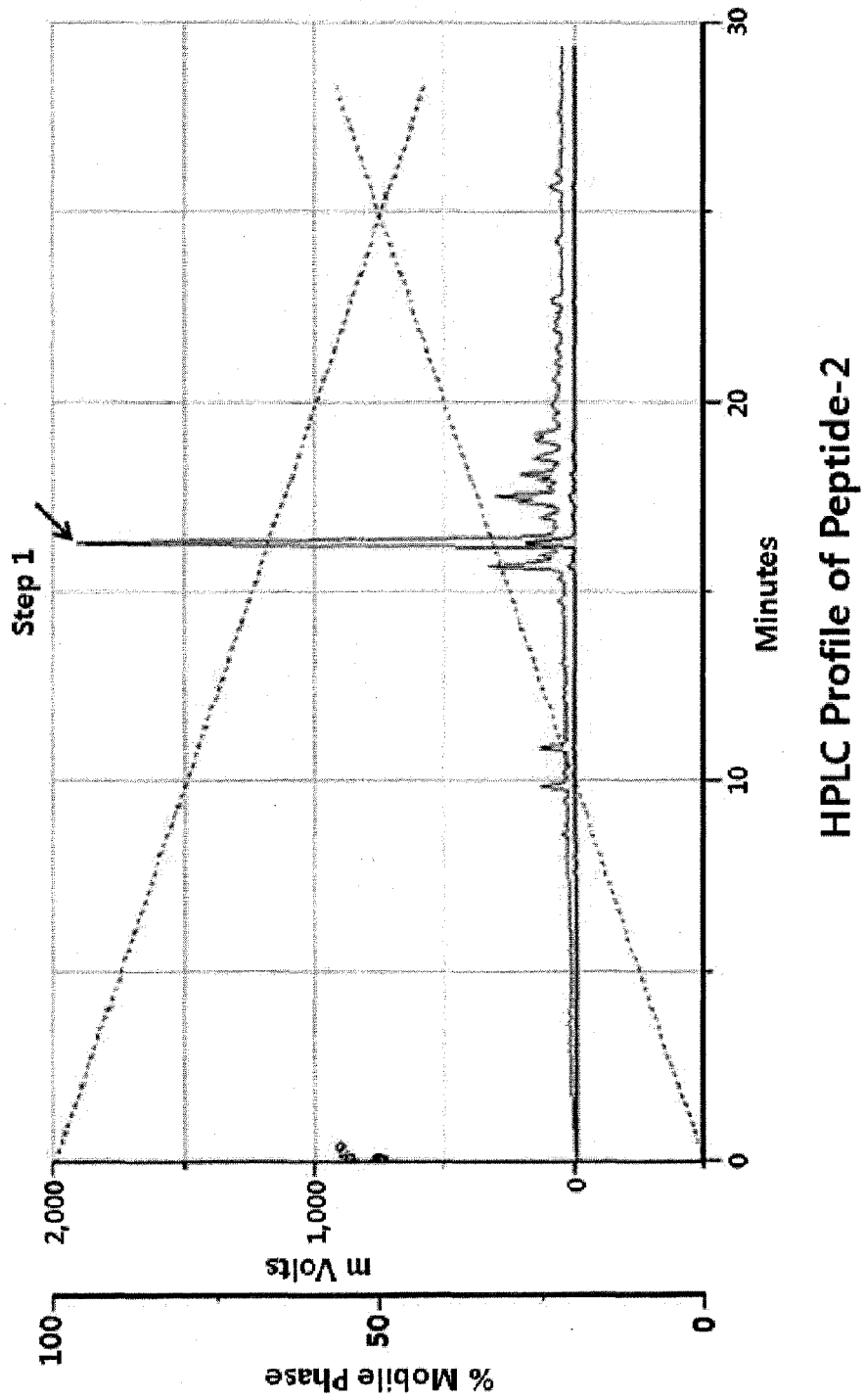
FIG. 2d represents a high performance liquid chromatography analysis of the peptide of SEQ ID NO:4 prepared in Example.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Synthesis of Ac-Tyr-Lys-Ser-Lys-Lys-Gly-Gly-Trp-Thr-His (SEQ ID NO:1)

700 mg of chloro trityl chloride resin (CTL resin, Nova Biochem Cat No. 01-64-0021) introduced into a reactor were added 10 ml of methylene chloride (MC) and agitated for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-His(Trt)-OH and 400 mmole of diisopropyl ethylamine (DIEA) were then added to the reactor, after which the mixture was dissolved by agitation and reaction was then undertaken with agitating for 1 hr. After reaction, the resultant was washed and reacted for 10 min in methanol and DIEA (2:1) dissolved in DCM, followed by washing with excess DCM/DMF (1:1). After the removal of the solvent, 10 ml of DMF were added to the reactor and agitated for 3 min, followed by removing the solvent. 10 ml of a deprotection solution (20% piperidine/DMF) were added to the reactor and agitated for 10 min at room temperature, and solution removal was performed. After adding the same volume of the deprotection solution, the reaction was undertaken for 10 min and solution was removed, followed by washing sequentially with DMF (twice), MC and DMF to yield His-(Trt)-CTL resins. 10 ml of DMF solution was added to a new reactor and then 200 mmole of Fmoc-Thr(tBu)-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acid solution was introduced into the reactor containing the deprotected resin and reaction was undertaken with agitating for 1 hr at room temperature. Following the removal of the reaction solution, the resultant was agitated three times with DMF solution for 5 min to remove unreacted residuals. A small amount of the reacted resin was taken to evaluate extent of reactions by Ninhydrine test. Using the deprotection solution, the deprotection was performed twice in the same manner as described above to yield Thr(tBu)-His-(Trt)-CTL resins. After washing with DMF and MC, Ninhydrine test was carried out and then the attachments of amino acids were performed as described above. Based on the amino acid sequence depicted in FIG. 1, Fmoc-Trp, Fmoc-Gly, Fmoc-Gly, Fmoc-Lys(Boc), Fmoc-Lys(Boc), Fmoc-Ser(tBu), Fmoc-Lys(Boc) and Fmoc-Tyr(tBu) were sequentially attached to resins. Fmoc-protecting group was removed by incubating with the deprotection solution twice for 10 min. For acetylation, acetic anhydride, DIEA and HoBt were incubated with the peptidyl resins twice for 1 hr, and the prepared peptidyl resins were washed three times sequentially with DMF, MC and methanol, dried under the flow of nitrogen gas, completely dried by vacuum-drying under $P_2O_5$ and then reacted with 30 ml of the leaving solution [containing 81.5% TFA (trifluoroacetic acid), 5% distilled water, 5% thioanisole, 5% phenol, 2.5% EDT and 1% TIS] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was dried under nitrogen atmosphere to provide 1.18 g of unpurified Ac-YKSKKGGWTH of SEQ ID NO:1 (yield rate, 72.6%). The molecular weight of the final product was determined as 1233.8 (theoretical MW 1233.4) using a mass analyzer.

Preparation Example 2

Synthesis of Other Peptides

The peptides of SEQ ID NOs:2-4 were synthesized as processes described in Preparation Example 1. SEQ ID NO:2 (Tyr-Ile-Ser-Lys-Lys-His-Ala-Gly-Lys-Asn-Trp-Phe: YISKKHAGKNWF) corresponds to amino acids 111-122 of aFGF, SEQ ID NO:3 (Asp-Ser-His-Thr-Gln-Tyr-Cys-Phe-His-Gly-Thr: DSHTQYCFHGT) to amino acids 10-20 of TGF-α, and SEQ ID NO:4 (Gly-Tyr-Val-Gly-Val-Arg-Cys-Glu-Ala-Ala-Asp-Leu-Asp-Ala: GYVGVRCEAADLDA) to amino acids 38-49 of TGF-α. The determined molecular weights of the peptides are summarized in Table 1:

TABLE 1

| SEQ | | Analyzed values(mass analyzer) | |
| ID NO | Amino acid sequence | Analyzed values | Theoretical values |
| --- | --- | --- | --- |
| 1 | Ac-YKSKKGGWTH | 1233.6 | 1233.4 |
| 2 | YISKKHAGKNWF | 1478.8 | 1478.7 |
| 3 | DSHTQYCFHGT | 1295.9 | 1295.4 |
| 4 | GYVGVRCEAADLDA | 1438.0 | 1437.6 |

Experimental Example 1

Influence of Peptides on Growth of HaCaT Keratinocytes and NIH3T3 Fibroblasts

In order to evaluate four peptides prepared in Preparation Examples 1-2 whether they have similar activities of growth factor-1, SRB (Sulforhodamine B; Sigma-Aldrich) colorimetric assay was carried out using HaCaT keratinocytes and NIH3T3 fibroblasts according to Rizzino et al. method (Rizzino, et al. Cancer Res., 48: 4266 (1988)).

HaCaT keratinocytes (The Korean Cell Line Bank) and NIH3T3 fibroblasts (The Korean Cell Line Bank) were cultured in 250 ml-flasks containing EMEM (Eagle's minimal essential media; Gibco, U.S.A.) supplemented with 10% FBS (fetal bovine serum). Cells cultured were treated with 0.25% trypsin solution to detach cells from the bottom of culture flasks and centrifuged to collect cell pellets. After cells were resuspended in EMEM not containing FBS, its aliquot ($4 \times 10^3$ cells) was added to each well of 96-well plates and cultured under 7% $CO_2$ for 24 hr at 37° C. After 24-hr culture, the medium was changed with a fresh medium not containing serum and cells were incubated with human aFGF (NIBSC, UK) or four peptides synthesized (10 ng/ml or 1,000 ng/ml) dissolved in water and 10% DMSO for 72 hr under the same conditions as described above. After removing supernatants, cells were washed once using PBS (phosphate buffered saline) and incubated with SRB solution. Cells were sufficiently washed with PBS and observed under a microscope to find cell viability. In addition, absorbance at 590 nm was measured to analyze cell proliferation.

Figure 3A:
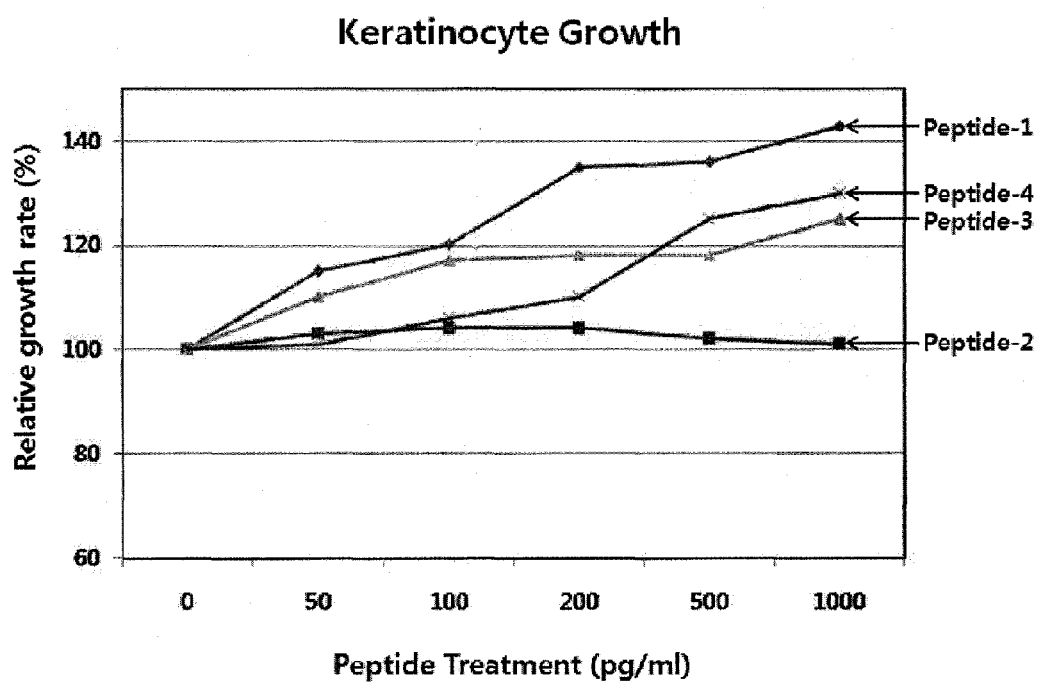
FIG. 3a is a graph representing a stimulatory effect on the growth of keratinocytes treated with the peptide of SEQ ID NOs:1-4 prepared in Example.
Figure 3B:
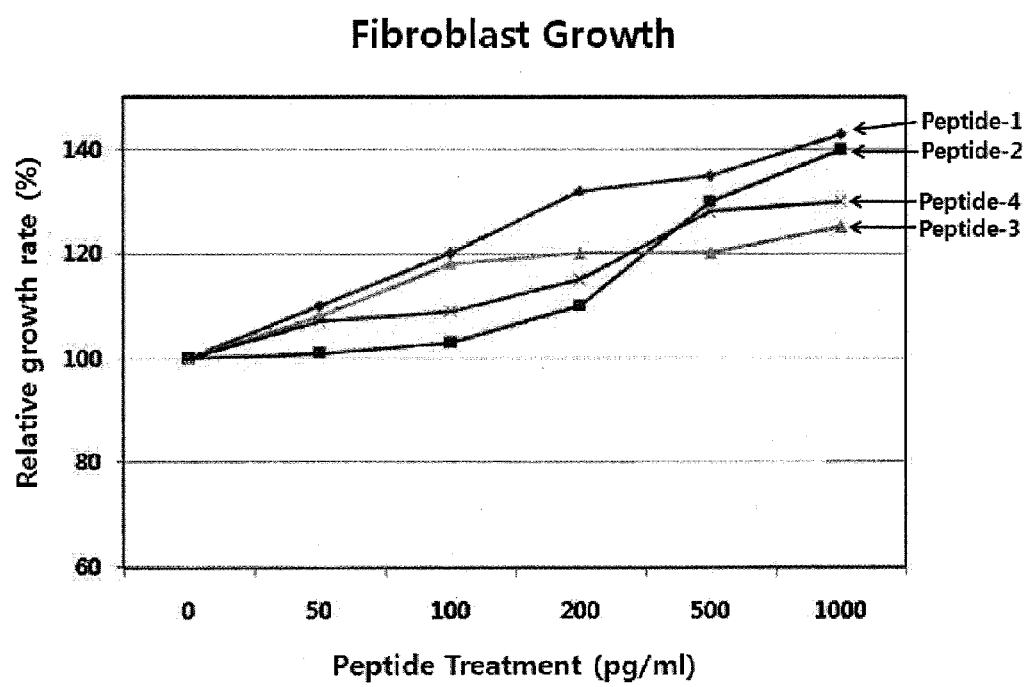
FIG. 3b is a graph representing a stimulatory effect on the growth of fibroblasts treated with the peptide of SEQ ID NOs:1-4 prepared in Example.
Figure 4:
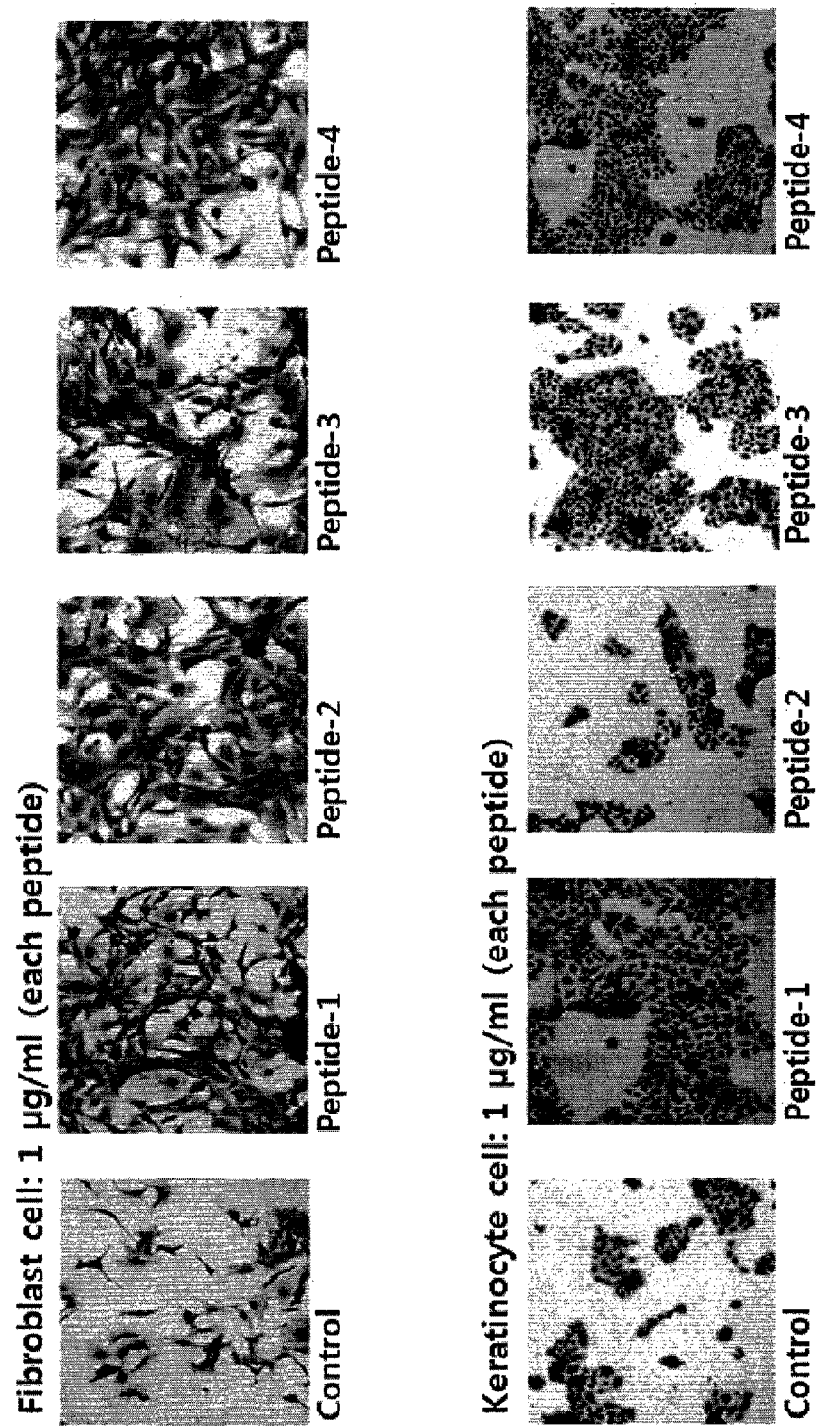
FIG. 4 is microscopic images representing a stimulatory effect on the growth of keratinocytes and fibroblasts treated with the peptide of SEQ ID NOs:1-4 prepared in Example.

FIG. 3a and FIG. 3b represent the analysis data for growth of keratinocytes and fibroblasts, respectively. FIG. 4 represents the growth pattern of keratinocytes and fibroblasts observed under microscope after 72 hr-treatment with peptides.

As shown in FIG. 3a, the four peptides of this invention dramatically promote growth of keratinocytes. Especially, the peptide 1, 3 and 4 of this invention were much better effects on growth of keratinocytes. In addition, as shown in FIG. 3b, it was observed that the peptides of this invention facilitate growth of fibroblasts. In particular, the peptide 1 and 2 of this invention had excellent effects on growth of fibroblasts. As represented in FIG. 4, the peptides of the present invention were revealed to significantly elevate growth of keratinocytes and fibroblasts.

Experimental Example 2

Influence of Peptides on Production of Collagen and Fibronectin

Figure 5A:
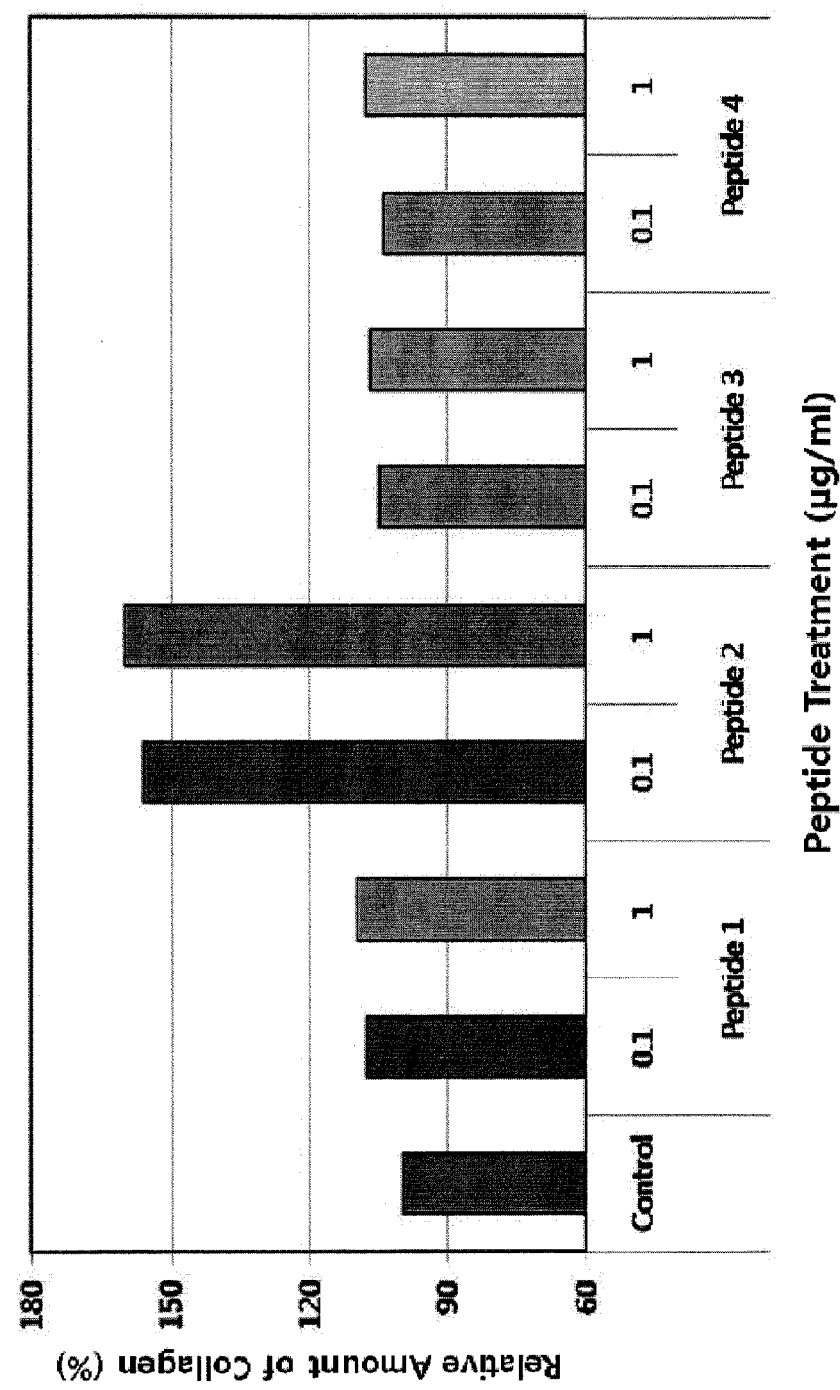
FIG. 5a represents a graph to show elevated collagen level in keratinocytes incubated with peptides of this invention (peptides 1-4).
Figure 5B:
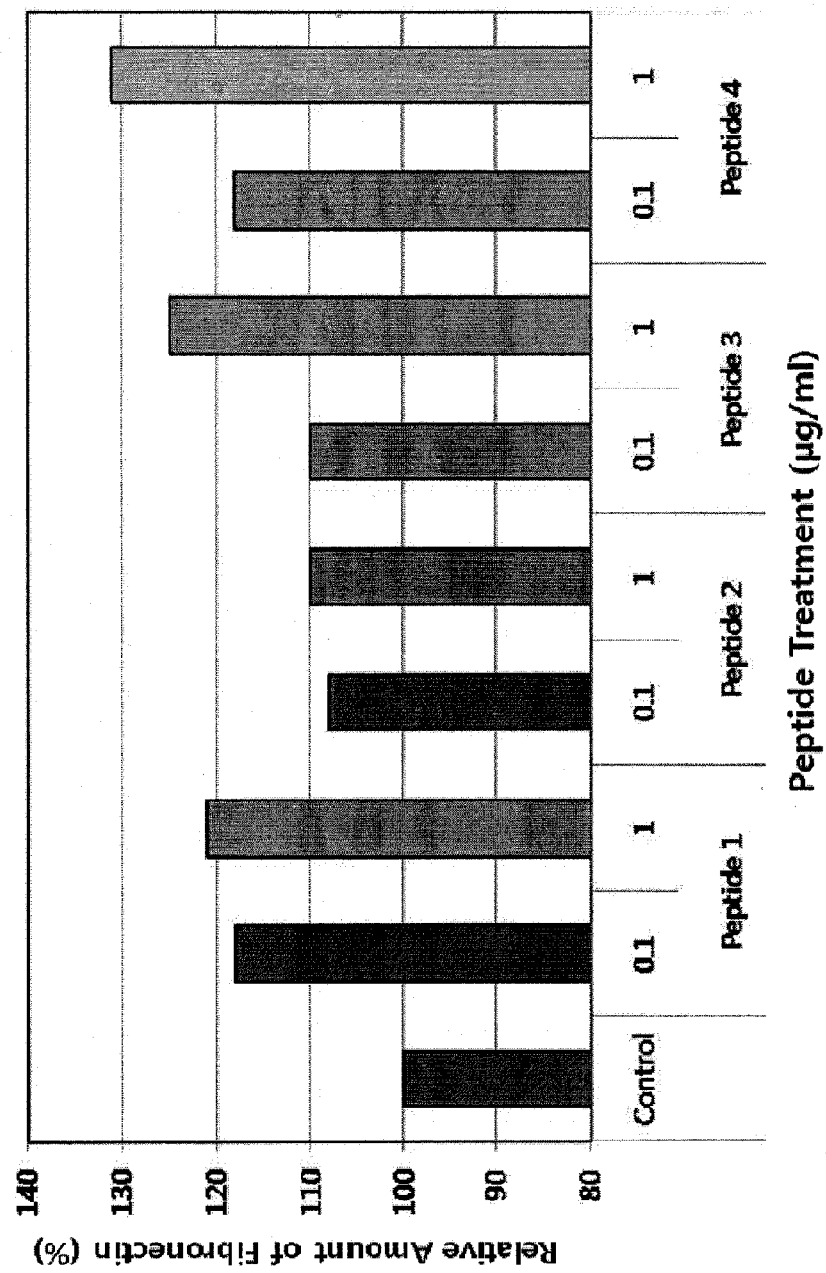
FIG. 5b represents a graph to show elevated fibronectin level in keratinocytes incubated with peptides of this invention (peptides 1-4).

HaCaT keratinocytes cultured for 48 hr were incubated with the peptides of the present invention for 72 hr. The levels of procollagen and fibronectin, indicators to show the improvement in skin wrinkle, were examined. The quantification was performed using Procollagen ELISA kit (Takara, Japan) and Fibronectin ELISA kit (CHEMICON, USA). As shown in FIG. 5a, the peptides of the present invention were revealed to elevate the level of procollagen in keratinocytes. First of all, the peptide 2 of the present invention was shown to remarkably promote the production of procollagen. In addition, as demonstrated in FIG. 5b, the peptides of the present invention were revealed to elevate the level of fibronectin in keratinocytes. Especially, the peptide 1 and 4 of the present invention were shown to strikingly facilitate the production of procollagen.

Taken together, these results demonstrate that the peptides of the present invention exhibit significant effects to improvement in skin conditions.

Experimental Example 3

Heat Stability of the Prepared Peptides

Figure 6:
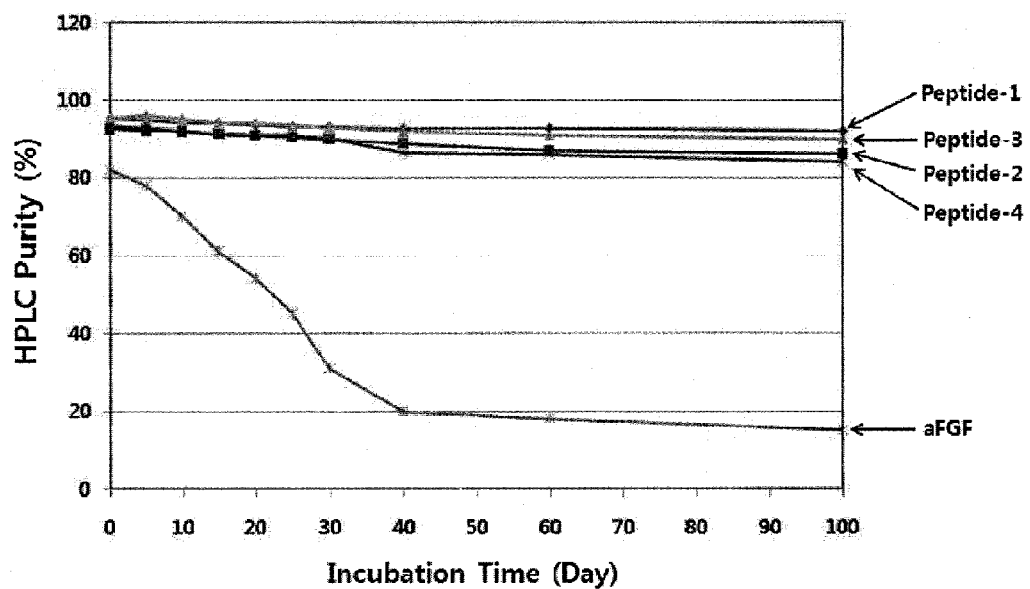
FIG. 6 is a graph comparing heat stability of the peptides of the present invention and natural-occurring aFGF.

Four peptides prepared in Preparation Examples 1-2 and standard products of growth factor (KGF, aFGF and TGF-α; NIBSC, UK) were dissolved in a phosphate buffer to a concentration of 0.11 mg/ml. The prepared solutions (1 ml) were introduced into glass vials and kept to stand at 37° C. Afterwards, the solutions were taken on days 0, 5, 10, 20, 25, 30, 40, 60 and 100, and centrifuged for removal of denatured peptides or proteins, followed by quantification using HPLC (FIG. 6). The residual amount of the prepared peptides was much higher than that of natural-occurring growth factors. The residual peptides as a sample were treated to cells according to the same method as described in Example 1, and subjected to MTT assay (Scudiero, D. A., et al. *Cancer Res.* 48: 4827-4833 (1988)) to determine residual activities of the peptide and natural-occurring growth factors. It could be appreciated that all peptides of the present invention have more superior activity than natural-occurring growth factors.

Example 1

Preparation of Nano Peptides 50 mg of the peptide synthesized in Preparation Examples was dissolved in 500 ml of distilled water by vigorous agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having 100-nm size. The nanosomes were prepared to have a final concentration of about 50 ppm and used as ingredients for cosmetics in alone or combination with others.

Formulation Example 1

Preparation of Skin Softener Using Nano Peptides

A skin softener containing one or more peptide nanosomes prepared in Example 1 was formulated according to the following composition:

TABLE 2

| Ingredients | Content (wt %) |
| --- | --- |
| Peptide nanosomes | 0.001 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |
| Benzophenone-9 | 0.05 |
| Perfume | Minute amount |
| Distilled water | Residual amount |
| Total | 100 |

Formulation Example 2

Preparation of Nutrient Cream Using Nano Peptides

A nutrient cream containing one or more peptide nanosomes prepared in Example 1 was formulated according to the following composition:

TABLE 3

| Ingredients | Content (wt %) |
| --- | --- |
| Peptide nanosomes | 0.001 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerine | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid containing one or more peptide nanosomes prepared in Example 1 was formulated according to the following composition:

TABLE 4

| Ingredients | Content (wt %) |
| --- | --- |
| Peptide nanosomes | 0.002 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Preparation of Essence Using Nano Peptides

An essence containing one or more peptide nanosomes prepared in Example 1 was formulated according to the following composition:

TABLE 5

| Ingredients | Content (wt %) |
| --- | --- |
| Peptide nanosomes | 0.005 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amout |
| Total | 100 |

Formulation Example 5

Hydrogel for Treating a Wound

Figure 7:
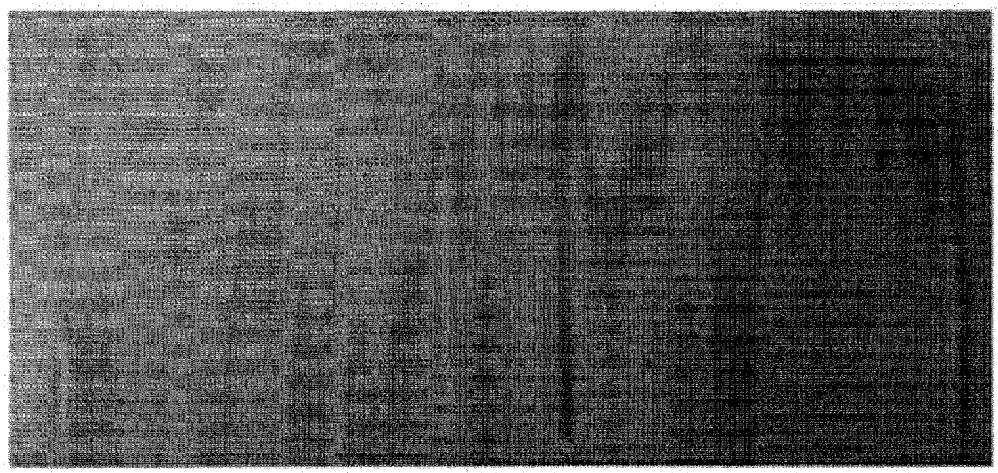
FIG. 7 represents a hydrogel image containing the peptides of the present invention.

A hydrogel patch containing one or more peptides prepared was formulated according to the following composition (FIG. 7). Hydrogel slices (1×1 cm$^2$) were prepared using a doctor blade and roller, and used in further experiments. Image of hydrogel slice was shown in FIG. 7.

TABLE 6

| Ingredients | Content (wt %) |
| --- | --- |
| Peptide nanosomes | 0.005 |
| Glycerin | 10.0 |
| 1,3-butylene glycol | 5.0 |
| Xanthan gum | 2.0 |
| Acrylate polymer | 23 |
| Agarose | 2 |
| Jojoba oil | 5 |
| Perfume, preservative, pigments | Proper amount |
| Distilled water | Residual amount |
| Total | 100 |

Experimental Example 4

Effects of Peptides on Wound Healing in Balb/C Mice

The hairs of the back portions of Balb/C male mice were completely removed using a hair cutter and subjected to injure a wound with a size between about 3 mm and 5 mm on their back using a disposable surgical blade. One day later, wound area of mice was topically administered with the prepared hydrogel patch containing one or more peptides and aFGF as a positive control, respectively. After three days, the equal amount of the hydrogel patch and aFGF was attached to the same wound area again. Seven days later, wound healing effects were observed in wound tissue of Balb/C mice by the naked eye (FIG. 8). As shown in FIG. 8. The wound healing effect was observed in the wound area administered with the prepared hydrogel patch containing one or more peptides by the naked eye compared with a non-treatment (negative control). Further, it could be distinguished by the naked eye that the wound area treated with the prepared hydrogel patch containing one or more peptide nanosomes was healed with the lapse of time much higher than that with aFGF. These results suggest that the peptides of the present invention have superior stability in external body compared with natural-occurring growth factors, enabling to function in a wound area for a long time. In addition, it could be appreciated that nanosome cosmetics and hydrogel comprising the peptides of the present invention exert significant improvements in skin and excellent efficacies on the treatment of wounds as they may have an activity of growth factor and an enhanced in vivo half-life.

Having described a preferred embodiment of the present invention, it is to be understood that variants and modifications thereof falling within the spirit of the invention may become apparent to those skilled in this art, and the scope of this invention is to be determined by appended claims and their equivalents.

What claimed is:

1. A method for improving skin conditions, comprising administering to a subject a composition containing as an active ingredient a peptide comprising the amino acid sequence of SEQ ID NO:1.

2. The method according to claim 1, wherein the C-terminal of the peptide is modified to have a hydroxyl group (—OH) or an amino group (—NH$_2$).

3. The method according to claim 1, wherein the N-terminal of the peptide is protected with a protection group selected from the group consisting of acetyl group, fluorenyl methoxy carbonyl group, formyl group, palmitoyl group, myristyl group, stearyl group, and polyethylene glycol (PEG).

4. The method according to claim 1, wherein the improvement in the skin condition is improvement in wrinkle or skin elasticity, prevention of skin aging, prevention of hair loss, promotion of hair growth, improvement in skin moisture, the removal of dark spots, the treatment of acne, or wound healing.

* * * * *

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: Peptide 1 human keratinocyte growth factor
      (KGF)

<400> SEQUENCE: 1

Tyr Lys Ser Lys Lys Gly Gly Trp Thr His
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptide 2 human acidic fibroblast growth factor
      (aFGF)

<400> SEQUENCE: 2

Tyr Ile Ser Lys Lys His Ala Gly Lys Asn Trp Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Peptide 3 human transforming growth factor-a
      (TGF-a)

<400> SEQUENCE: 3

Asp Ser His Thr Gln Tyr Cys Phe His Gly Thr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide 4 human TGF-a

<400> SEQUENCE: 4

Gly Tyr Val Gly Val Arg Cys Glu Ala Ala Asp Leu Asp Ala
1               5                   10

<210> SEQ ID NO 5
<211> LENGTH: 163
<212> TYPE: PRT
<213> ORGANISM: Artificial Sequence
<220> FEATURE:
<223> OTHER INFORMATION: Synthetic Construct

<400> SEQUENCE: 5

Cys Asn Asp Met Thr Pro Glu Gln Met Ala Thr Asn Val Asn Cys Ser
1               5                   10                  15
```

```
Ser Pro Glu Arg His Thr Arg Ser Tyr Asp Tyr Met Glu Gly Gly Asp
         20                  25                  30

Ile Arg Val Arg Arg Leu Phe Cys Arg Thr Gln Trp Tyr Leu Arg Ile
         35                  40                  45

Asp Lys Arg Gly Lys Val Lys Gly Thr Gln Glu Met Lys Asn Asn Tyr
 50                  55                  60

Asn Ile Met Glu Ile Arg Thr Val Ala Val Gly Ile Val Ala Ile Lys
 65                  70                  75                  80

Gly Val Glu Ser Glu Phe Tyr Leu Ala Met Asn Lys Glu Gly Lys Leu
                 85                  90                  95

Tyr Ala Lys Lys Glu Cys Asn Glu Asp Cys Asn Phe Lys Glu Leu Ile
                100                 105                 110

Leu Glu Asn His Tyr Asn Thr Tyr Ala Ser Ala Lys Trp Thr His Asn
             115                 120                 125

Gly Gly Glu Met Phe Val Ala Leu Asn Gln Lys Gly Ile Pro Val Arg
         130                 135                 140

Gly Lys Lys Thr Lys Lys Glu Gln Lys Thr Ala His Phe Leu Pro Met
145                 150                 155                 160

Ala Ile Thr

<210> SEQ ID NO 6
<211> LENGTH: 154
<212> TYPE: PRT
<213> ORGANISM: Artificial Sequence
<220> FEATURE:
<223> OTHER INFORMATION: Synthetic Construct

<400> SEQUENCE: 6

Ala Glu Gly Glu Ile Thr Thr Phe Thr Ala Leu Thr Glu Lys Phe Asn
1               5                   10                  15

Leu Pro Pro Gly Asn Tyr Lys Lys Pro Lys Leu Leu Tyr Cys Ser Asn
                 20                  25                  30

Gly Gly His Phe Leu Arg Leu Leu Pro Asp Gly Thr Val Asp Gly Thr
             35                  40                  45

Arg Asp Arg Ser Asp Gln His Ile Gln Leu Gln Leu Ser Ala Glu Ser
 50                  55                  60

Val Gly Glu Val Tyr Ile Lys Ser Thr Glu Thr Gly Gln Tyr Leu Ala
 65                  70                  75                  80

Met Asp Thr Asp Gly Leu Leu Tyr Gly Ser Gln Thr Pro Asn Glu Glu
                 85                  90                  95

Cys Leu Phe Leu Glu Arg Leu Glu Glu Asn His Tyr Asn Thr Tyr Leu
                100                 105                 110

Ser Lys Lys His Ala Glu Lys Asn Trp Phe Val Gly Leu Lys Lys Asn
             115                 120                 125

Gly Ser Cys Lys Arg Gly Pro Arg Thr His Tyr Gly Gln Lys Ala Leu
         130                 135                 140

Leu Phe Leu Pro Leu Pro Val Ser Ser Asp
145                 150

<210> SEQ ID NO 7
<211> LENGTH: 50
<212> TYPE: PRT
<213> ORGANISM: Artificial Sequence
<220> FEATURE:
<223> OTHER INFORMATION: Synthetic Construct

<400> SEQUENCE: 7

Val Val Ser His Phe Asn Asp Cys Pro Asp Ser His Thr Gln Phe Cys
```

-continued

```
1               5                   10                  15

Phe His Ala Thr Cys Arg Phe Leu Val His Glu Asp Lys Pro Ala Cys
            20                  25                  30

Val Cys His Ser Gly Tyr Val Gly Ala Arg Cys Glu His Ala Asp Leu
        35                  40                  45

Leu Ala
    50
```